United States Patent [19]

Tsuchida et al.

[11] Patent Number: 5,284,757
[45] Date of Patent: Feb. 8, 1994

[54] PROCESS FOR PRODUCING L-ARGININE BY FERMENTATION WITH BREVIBACTERIUM OR CORYNEBACTERIUM

[75] Inventors: Takayasu Tsuchida; Noboro Ohtsuka; Hiroshi Takeuchi; Haruo Uchibori, all of Kawasaki, Japan

[73] Assignee: Ajinomoto Company, Inc., Tokyo, Japan

[21] Appl. No.: 51,433

[22] Filed: Apr. 23, 1993

Related U.S. Application Data

[63] Continuation of Ser. No. 463,464, Jan. 11, 1990, abandoned.

[30] Foreign Application Priority Data

Jan. 12, 1989 [JP] Japan ................... 64-5770

[51] Int. Cl.$^5$ .................... C12P 13/10; C12N 1/00
[52] U.S. Cl. .................... 435/114; 435/840; 435/843
[58] Field of Search ................ 435/114, 840, 843

[56] References Cited

U.S. PATENT DOCUMENTS

| | | | |
|---|---|---|---|
| 3,878,044 | 4/1975 | Kubota et al. | 435/114 |
| 3,956,275 | 5/1976 | Demain et al. | 435/81 |
| 3,993,544 | 11/1976 | Demain et al. | 435/81 |
| 4,264,737 | 4/1981 | Murphy | 435/172.1 |
| 4,366,247 | 12/1982 | Baltz et al. | 435/124 |
| 4,490,467 | 12/1984 | Jarman | 435/101 |
| 4,775,623 | 10/1988 | Katsumata et al. | 435/114 |
| 5,017,482 | 5/1991 | Katsumata et al. | 435/114 |

*Primary Examiner*—David M. Naff
*Assistant Examiner*—Michael V. Meller
*Attorney, Agent, or Firm*—Oblon, Spivak, McClelland, Maier & Neustadt

[57] ABSTRACT

L-arginine is produced in high yields by culturing a microorganism of the genus Brevibacterium or the genus Cornyebacterium, which is resistant to a compound of the formula X-guanidine, wherein X is an aliphatic group or derivative thereof. The preferred microorganisms are *Brevibacterium flavum* FERM BP-2227 and *Corynebacterium glutamicum* FERM BP-2228.

2 Claims, No Drawings

PROCESS FOR PRODUCING L-ARGININE BY FERMENTATION WITH BREVIBACTERIUM OR CORYNEBACTERIUM

This application is a continuation of application Ser. No. 07/463,464, filed Jan. 11, 1990, now abandoned.

BACKGROUND OF THE INVENTION

1. Field of the Invention

The present invention relates to a process for producing L-arginine by fermentation and strains of microorganisms which produce L-arginine in high yield.

2. Discussion of the Background

L-Arginine is an important component of drugs for stimulating liver functions, amino acid infusion, total amino acid preparations, etc. To reduce the production costs of L-arginine, it is important to improve the fermentation yield. In order for microorganisms belonging to the genus Brevibacterium or the genus Corynebacterium to exhibit L-arginine productivity, it is known that a resistance to 2-thiazolealanine (hereafter simply referred to as 2-TA), arginine hydroxamate, etc. should be imparted to the microorganism. It is also known that the production of L-arginine is improved by imparting sulfa agent or argininol resistance, resistance to chemicals such as 8-azaguanine, α-amino-β-hydroxyvaleric acid, etc., in addition to the chemical resistance described above, and by imparting auxotrophy for amino acids such as L-histidine, L-proline, L-threonine, L-tryptophan, L-lysine, etc.

However, use of the conventional L-arginine-producing strains of microorganisms results in an unsatisfactory yield of L-arginine. Thus, there remains a need for a process for producing L-arginine by fermentation in high yield. There also remains a need for strains of microorganisms which produce L-arginine in high yield by fermentation.

SUMMARY OF THE INVENTION

Accordingly, one object of the present invention is to provide a process for producing L-arginine by fermentation in high yield.

Another object of the present invention is to provide strains of microorganisms which produce L-arginine in high yield by fermentation.

These and other objects, which will become apparent during the course of the following detailed description, have been achieved by the inventors' discovery that strains of the genus Brevibacterium or the genus Corynebacterium to which a resistance to X-guanidine, in which X is an aliphatic group or a derivative of an aliphatic group, (hereafter simply referred to as X-GN) has been imparted are capable of producing L-arginine in a higher yield than in conventional L-arginine-producing strains.

That is, in one embodiment, the present invention relates to a process for producing L-arginine which comprises culturing an L-arginine-producing microorganism belonging to the genus Brevibacterium or the genus Cornyebacterium and having X-GN resistance in a liquid medium, for a sufficient time to accumulate L-arginine in the culture, and collecting the L-arginine from the culture.

DETAILED DESCRIPTION OF THE PREFERRED EMBODIMENTS

The microorganisms used in the present invention are variants belonging to the genus Brevibacterium or the genus Corynebacterium, having X-GN resistance and capable of producing L-arginine. To obtain the variants of the present invention, L-arginine productivity may previously be imparted to wild strains described below and X-GN resistant may then be imparted thereto; alternatively, X-GN resistance may be first imparted and L-arginine productivity may then be imparted.

Suitable X-GN compounds include those in which X is an aliphatic group or derivative thereof. Suitable aliphatic groups include branched or unbranched alkyl groups, branched or unbranched alkenyl groups, and branched or unbranched alkynyl groups. Specific examples of suitable X-GN compounds include butenylguanidine, hexylguanidine, octylguanidine, and 4-methyl-3-butenylguanidine, etc.

Suitable wild strains which may be used as parent strains of the variants of the present invention are bacteria belonging to the genus Brevibacterium or the genus Cornyebacterium, especially a Coryneform producing L-glutamic acid, and are exemplified by the following bacteria:

Brevibacterium divaricatum ATCC 14020
Brevibacterium flavum ATCC 14067
Brevibacterium lactofermentum ATCC 13869
Brevibacterium saccharolyticum ATCC 14066
Corynebacterium acetoacidophilum ATCC 13870
Cornyebacterium glutamicum ATCC 13032

For the mutation of these parent strains to the variants of the present invention, a conventional method of mutation which comprises contacting these strains with N-methyl-N'-nitro-N''-nitrosoguanidine, etc. may be suitably used. Isolation of the variants of the present invention may be effected by collecting the strains which can be grown in a medium containing X-GN.

In many cases, the yield increases by further imparting to the aforesaid variants properties already known to improve the productivity of L-arginine, such as sulfaguanidine resistance, argininol resistance or 8-azaguanine resistance.

The media used for culturing the present variants can be any conventional media containing carbon sources, nitrogen sources, inorganic ions, substances satisfying the auxotrophy described above and, if necessary, other organic trace nutrients including vitamins, etc.

As carbon sources, there are preferably used carbohydrates such as glucose, sucrose, etc., organic acids such as acetic acid, etc. As nitrogen sources, there are preferably used ammonia water, ammonia gas, ammonium salts, etc. As inorganic ions, potassium ions, sodium ions, magnesium ions, phosphate ions, and the like are appropriately added to media, as required.

Incubation is preferably conducted under aerobic conditions. When the incubation is carried out while adjusting the pH of the medium to a range of from 4 to 8, preferably 5 to 7.5 at a temperature of from 25° to 37° C., preferably 28° to 34° C., better results can be obtained. Thus, when cultured for 1 to 7 days, remarkable amounts of L-arginine are produced and accumulated in the media.

For collecting L-arginine from the culture solution, any conventional method, such as a method using an ion exchange resin, etc. can be used.

Other features of the invention will become apparent in the course of the following descriptions of exemplary embodiments which are given for illustration of the invention and are not intended to be limiting thereof.

EXAMPLES

An example for the mutation of parent strains to the variants of the present invention and the relationship between the concentration of octylguanidine (hereafter simply referred to as O-GN) as X-GN and growth of the present strains are shown below.

Method for Mutation

Bacterial cells of *Brevibacterium flavum* AJ 11169, FERM P-4161 (2-TA resistant strain derived from ATCC 14067) and *Corynebacterium glutamicum* AJ 12092, FERM P-7273 (2-TA resistant strain derived from ATCC 13032), which had been grown in bouillon agar slants at 30° C. for 24 hours, were each suspended in M/30 phosphate buffer solutions at a cell density of $10^8$ to $10^9$/ml. To the cell suspensions was added 500 μg/ml of N-methyl-N'-nitro-N"-nitrosoguanidine. The mixtures were maintained at 30° C. for 20 minutes. Then the cells were collected by centrifugation. After thoroughly washing with M/30 phosphate buffer solution, the cells were inoculated on a medium having the composition shown in Table 1 and cultured at 31.5° C for 4 to 10 days.

TABLE 1

| Composition of Medium (pH 7.0) | |
|---|---|
| Component | Content |
| Glucose | 1.0 g/dl |
| Urea | 0.2 g/dl |
| KH$_2$PO$_4$ | 0.1 g/dl |
| MgSO$_4$.7H$_2$O | 0.1 g/dl |
| FeSO$_4$.7H$_2$O | 0.002 g/dl |
| MnSO$_4$.7H$_2$O | 0.002 g/dl |
| Biotin | 100 μg/l |
| Thiamine hydrochloride | 100 μg/l |
| O-GN | 0.1 g/dl |
| Agar | 2.0 g/dl |

From the strains grown in the agar medium, *Brevibacterium flavum* AJ 12429 (2-TA resistant, O-GN resistant) and *Corynebacterium glutamicum* AJ 12430 (2-TA resistant, O-GN resistant) which exhibited a high productivity of L-arginine were obtained. *Brevibacterium flavum* AJ 12429 and *Corynebacterium glutamicum* 12430 have both been deposited with the Fermentation Research Institute, Agency of Industrial Science and Technology, Ministry of International Trade and Industry, 1-3, Higashi 1-chome, Tsukuba-shi, Ibaraki-ken 305, Japan under the provisions of the Budapest Treaty on Dec. 12, 1988 and can be accessed under the identification numbers FERM BP-2227 and FERM BP-2228, respectively.

The O-GN resistance of the thus-obtained variants was compared with that of the parent strains.

Onto media composed of 0.5 g/dl of glucose, 0.15 g/dl of urea, 0.15 g/dl of ammonium sulfate, 0.31 g/dl of KH$_2$PO$_4$, 0.1 g/dl of K$_2$HPO$_4$, 0.01 g/dl of MgSO$_4$.7H$_2$O, 0.1 mg/dl of CaCl$_2$.2H$_2$O, 100 μg/l of biotin, 100 μg/l of thiamine hydrochloride, 0.002 g/dl of FeSO$_4$.7H$_2$O, 0.002 g/dl of MnSO$_4$.7H$_2$O and O-GN in the amounts shown in Table 2, adjusted to a pH of 7.0, there were inoculated suspensions of the cells in sterile water, which were obtained by culturing in natural medium (1 g/dl of peptone, 1 g/dl of yeast extract and 0.5 g/dl of NaCl, pH 7.0) in slants for 24 hours. After culturing for 24 hours, the degree of growth was determined in terms of turbidity.

TABLE 2

| Strain | Concentration of O-GN (μg/ml) | | | | |
|---|---|---|---|---|---|
| | 0 | 25 | 50 | 100 | 200 |
| *Brevibacterium flavum* AJ 11169 (FERM P-4161) | 0.90 | 0.50 | 0.10 | 0 | 0 |
| *Brevibacterium flavum* AJ 12429 (FERM BP-2227) | 0.85 | 0.85 | 0.70 | 0.30 | 0 |
| *Corynebacterium glutamicum* AJ 12092 (FERM P-7273) | 0.95 | 0.70 | 0.15 | 0 | 0 |
| *Corynebacterium glutamicum* AJ 12430 (FERM BP-2228) | 0.95 | 0.96 | 0.90 | 0.60 | 0.10 |

As shown by the results presented above, the strains according to the present invention possess a resistance to X-GN and are thus able to grow at higher concentrations of O-GN than the parent strains.

EXAMPLE

Production of L-Arginine

A medium containing 10 g/dl of glucose, 7 g/dl of (NH$_4$)$_2$SO$_4$, 0.1 g/dl of KH$_2$PO$_4$, 0.04 g/dl of MgSO$_4$.7H$_2$O, 1 mg/dl of FeSO$_4$.7H$_2$O, 1 mg/dl of MnSO$_4$.4H$_2$O, 100 μg/l of thiamine. HCl, 100 μg/l of biotin, 60 mg of soybean protein acid hydrolysate (calculated as total nitrogen) and 5 g/dl of calcium carbonate (separately sterilized) was adjusted to pH 7.0, and 20 ml of the medium was charged in flasks with a shoulder having a 500 ml volume followed by sterilization with heating. One platinum loop of each of the strains shown in Table 2 was inoculated on the medium in separate flasks and shaken for 4 days while maintaining the temperature at 31.5° C. L-Arginine was produced and accumulated in the culture solution of each strain in the amount shown in Table 3.

TABLE 3

| Strain | Resistance Properties | Amount of L-Arginine Accumulated (g/dl) |
|---|---|---|
| *Brevibacterium flavum* AJ 11169 (FERM P-4161) | 2-TA$^r$ | 1.9 |
| *Brevibacterium flavum* AJ 12429 (FERM BP-2227) | 2-TA$^r$, O-GN$^r$ | 3.6 |
| *Corynebacterium glutamicum* AJ 12092 (FERM P-7273) | 2-TA$^r$ | 1.7 |
| *Corynebacterium glutamicum* AJ 12430 (FERM BP-2228) | 2-TA$^r$, O-GN$^r$ | 3.4 |

2-TA$^r$: 2-thiazolealanine resistance
O-GN$^r$: octylguanidine resistance

As clearly shown by the results presented above, the present strains, which possess a resistance to X-GN, produce L-arginine in a higher yield than strains which are not resistant to X-GN.

AJ 12429 was cultured by the method described above to give 1 liter of the culture solution. The culture solution was centrifuged to remove the cells and the like. The supernatant was passed through a weakly acidic ion exchange resin "Amberlite" C-50 (NH$_4$ type). After washing the resin with water, L-arginine was eluted with 2 N NH$_4$OH and the eluate was concentrated. From the concentrate, 19.5 g of L-arginine was obtained as crude crystals.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A process for producing L-arginine comprising: culturing *Brevibacterium flavum* FERM BP-2227 in a nutrient medium containing assimilable sources of carbon, nitrogen and inorganic salts under conditions to produce L-arginine, and recovering L-arginine.

2. A process for producing L-arginine comprising: culturing *Corynebacterium glutamicum* FERM BP-2228 in a nutrient medium containing assimilable sources of carbon, nitrogen and inorganic salts under conditions to produce L-arginine, and recovering L-arginine.

* * * * *